(12) United States Patent
Drobyshev et al.

(10) Patent No.: US 11,358,911 B2
(45) Date of Patent: Jun. 14, 2022

(54) LOW-ENERGY CONSUMPTION METHOD FOR DEHYDRATING ETHANOL INTO ETHYLENE

(71) Applicants: IFP Energies nouvelles, Rueil-Malmaison (FR); TOTAL RESEARCH & TECHNOLOGY FELUY, Seneffe (BE)

(72) Inventors: Kirill Drobyshev, Rueil-Malmaison (FR); Vincent Coupard, Rueil-Malmaison (FR); Nikolai Nesterenko, Nivelles (BE); Jean-Christophe Gabelle, Rueil-Malmaison (FR)

(73) Assignees: IFP Energies nouvelles, Rueil-Malmaison (FR); TOTAL RESEARCH & TECHNOLOGY FELUY, Seneffe (BE)

( * ) Notice: Subject to any disclaimer, the term of this patent is extended or adjusted under 35 U.S.C. 154(b) by 0 days.

(21) Appl. No.: 17/413,080

(22) PCT Filed: Nov. 27, 2019

(86) PCT No.: PCT/EP2019/082717
§ 371 (c)(1),
(2) Date: Jun. 11, 2021

(87) PCT Pub. No.: WO2020/120136
PCT Pub. Date: Jun. 18, 2020

(65) Prior Publication Data
US 2022/0041525 A1    Feb. 10, 2022

(30) Foreign Application Priority Data
Dec. 14, 2018   (FR) .................................... 1872972

(51) Int. Cl.
*C07C 1/24* (2006.01)
*B01J 19/24* (2006.01)

(52) U.S. Cl.
CPC ............... *C07C 1/24* (2013.01); *B01J 19/242* (2013.01); *B01J 2219/00123* (2013.01);
(Continued)

(58) Field of Classification Search
CPC ...... C07C 1/24; C07C 2529/40; B01J 19/242; B01J 2219/00123; B01J 2219/00128; B01J 2219/00162
See application file for complete search history.

(56) References Cited

U.S. PATENT DOCUMENTS

| 4,232,179 A | 11/1980 | Valladares et al. |
| 2013/0190547 A1* | 7/2013 | Coupard ................... C07C 7/04 585/639 |

FOREIGN PATENT DOCUMENTS

WO    2013011208 A1    1/2013

OTHER PUBLICATIONS

International Search Report for PCT/EP2019/082717 dated Mar. 13, 2020.

* cited by examiner

*Primary Examiner* — Thuan D Dang
(74) *Attorney, Agent, or Firm* — Millen White Zelano & Branigan, PC; Brion P. Heaney

(57) ABSTRACT

A process for dehydrating an ethanol feedstock to give ethylene, includes:
a) a vaporization stage;
b) a heating stage;
c) a dehydration stage in a multitubular reactor comprising tubes having a length of between 2 and 4 m, said tubes comprising a, preferably zeolitic, dehydration catalyst, the feedstock having an inlet temperature of greater than 400° C.

(Continued)

and less than 550° C. and an inlet pressure of between 0.8 and 1.8 MPa, the heat transfer fluid having an inlet temperature of greater than 430° C. and less than 550° C. and a mass flow rate such that the ratio of the mass flow rates of the heat transfer fluid relative to the feedstock is greater than or equal to 10;

d) separation into an effluent comprising ethylene and an aqueous effluent;

e) purification of the aqueous effluent and separation of a stream of purified water and a stream of unconverted ethanol.

24 Claims, 1 Drawing Sheet

(52) U.S. Cl.
CPC ............... *B01J 2219/00128* (2013.01); *B01J 2219/00162* (2013.01); *C07C 2529/40* (2013.01)

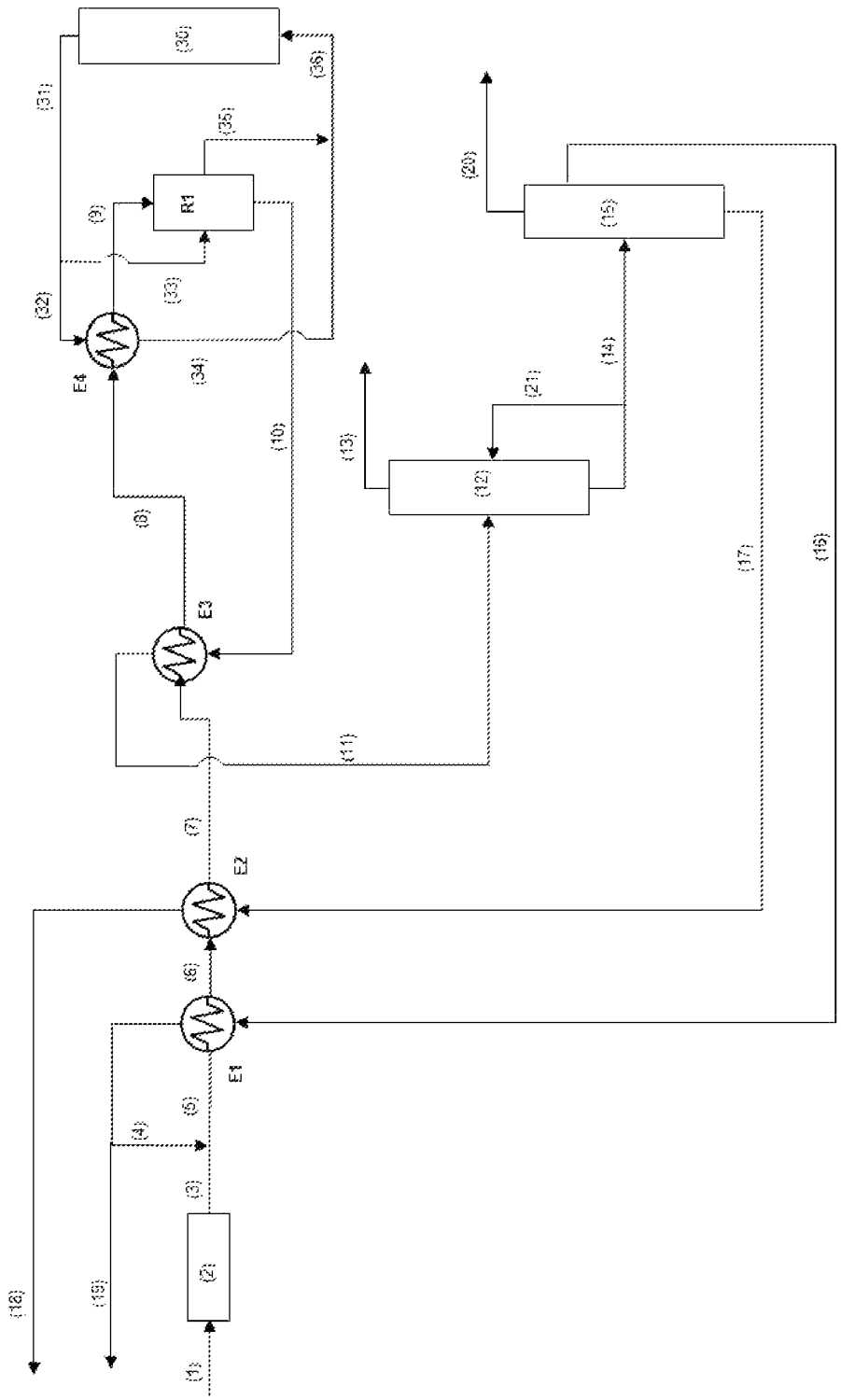

LOW-ENERGY CONSUMPTION METHOD FOR DEHYDRATING ETHANOL INTO ETHYLENE

FIELD OF THE INVENTION

The present invention relates to a process for transforming ethanol into ethylene and in particular to a process for dehydrating ethanol.

PRIOR ART

The dehydration reaction of ethanol to give ethylene has been known and described in detail since the end of the 19th century. "The Dehydration of Alcohols over Alumina. I:The reaction scheme", H. Knozinger, R. Kohne, Journal of Catalysis (1966), 5, 264-270 is considered to be the fundamental publication on studies of the dehydration of alcohols such as ethanol. It is known that this reaction is a highly endothermic equilibrium reaction with an equilibrium shifted towards ethylene at high temperature. The temperature drop corresponding to the total conversion of pure ethanol in an adiabatic reactor is 380° C. At lower temperature, the ethanol is converted into diethyl ether (DEE). This reaction "intermediate" may be present in ethylene dehydration processes in which the conversion is partial or between two reactors in multi-reactor processes. DEE can then be converted into ethylene at higher temperature. The reference catalyst often used is a monofunctional acid catalyst, gamma-alumina being the most cited catalyst. Zeolites are also used for this application, in particular ZSM5 since the 1980s, such as for example in "Reactions of ethanol over ZSM-5", S.N. Chaudhuri & al., Journal of Molecular Catalysis 62:289-295 (1990).

U.S. Pat. No. 4,232,179 describes a process for dehydrating ethanol to give ethylene in which the heat needed for the reaction is supplied by the introduction, into the reactor, of a heat transfer fluid as a mixture with the feedstock. The heat transfer fluid is either steam originating from an external source, or an external stream originating from the process, or the recycle of a portion of the effluent of the dehydration reactor, that is to say the ethylene produced. The introduction of the mixture of the feedstock with said heat transfer fluid makes it possible to supply the heat needed to maintain the temperature of the catalytic bed at a level compatible with the desired conversions. In the case where the heat transfer fluid is the effluent of the dehydration reactor, a compressor for recycling said effluent is necessary. However, recycling the ethylene produced by the reaction is a disadvantage since the introduction of the ethylene changes the equilibrium of the dehydration reaction. In addition, the ethylene takes part in side reactions of oligomerization, of hydrogen transfer and of disproportionation of the olefins which are reactions of order greater than 0 with respect to their reactant. The increase in the concentration of ethylene starting from the beginning of the reaction increases the formation of byproducts. The loss of ethylene is therefore more significant, which results in a drop in selectivity.

Patent application WO 2007/134415 describes a process for dehydrating ethanol to give ethylene which is improved with respect to that of the patent U.S. Pat. No. 4,232,179, enabling a reduced investment cost by virtue of a reduced amount of equipment and reduced operational costs, by virtue of the lack of use of steam external to the process. In this process, at least a portion of the effluent of the dehydration reactor (mixture of ethylene produced and steam) and of the superheated steam obtained from the water produced by the dehydration of ethanol and condensed in the reactor are used as heat transfer fluid and enter into the dehydration reactor as a mixture with the ethanol. Said patent application makes no mention of the pressure conditions to be observed between the ethanol feedstock and the effluent for the purpose of maximizing heat exchange.

U.S. Pat. No. 4,396,789 also describes a process for dehydrating ethanol to give ethylene in which ethanol and steam acting as heat transfer fluid are introduced into the first reactor at a temperature of between 400 and 520° C. and at a high pressure of between 20 and 40 atm, such that the effluent produced by the dehydration reaction is withdrawn from the final reactor at a pressure at least greater than 18 atm, said reaction product, i.e. ethylene, possibly undergoing after cooling the final cryogenic distillation stage without an intermediate compression stage. Said process is also characterized by an exchange of heat between said product of the dehydration reaction and the feedstock introduced into the first reactor, said reaction product being used to vaporize the feedstock entering the first reactor. The unconverted ethanol, at least a portion of the water formed during the reactions of the process and the water added for the final washing of the gases are recycled to ensure the complete conversion of the ethanol.

Patent application WO 2011/002699 discloses a process for dehydrating an ethanol feedstock to give ethylene comprising the vaporization of a mixture of ethanol and of water and the reaction of this mixture in an adiabatic reactor. This application does not address the problem of maximizing the recovery of heat for the purpose of reducing the energy consumption of the process.

Patent application WO 2013/011208 discloses a process for dehydrating an ethanol feedstock to give ethylene comprising thermal integration of the streams resulting from the reaction unit in which the dehydration reaction proceeds in adiabatic reactors. The dehydration process described in patent application WO 2014/083260 comprises in addition stages of preheating and of pretreating the ethanol feedstock, before the stages of vaporization, of compression and of reaction in the adiabatic reactors. In these processes, the exchanges of heat between the different streams are promoted, thus limiting energy consumption. However, the processes of these applications use in particular a succession of adiabatic reactors between which the effluents are heated in order to maintain a temperature of the reaction stream sufficient to achieve an optimal conversion rate.

Patent application WO 2018/046515 for its part describes a process for dehydrating isobutanol to give butene comprising a simultaneous dehydration and isomerization stage carried out in particular under isothermal or pseudo-isothermal conditions at a temperature of 300° C. or 350° C. in multitubular fixed-bed reactors.

An objective of the invention is to provide a process for dehydrating ethanol to give ethylene of high purity, said process making it possible to retain the high selectivity for ethylene with a specific energy consumption per ton of produced ethylene which is significantly lowered compared to prior art processes.

Another objective of the invention is to provide a process for dehydrating ethanol to give ethylene, making it possible to achieve high ethanol conversion rates while at the same time reducing the temperature of the feedstock at the inlet into the reaction unit.

SUMMARY AND ADVANTAGE OF THE INVENTION

The invention relates to a process for dehydrating an ethanol feedstock to give ethylene, comprising:

a) a stage for vaporizing a vaporization feedstock comprising said ethanol feedstock in an exchanger by means of a heat exchange with a dehydration effluent resulting from stage c), so as to produce a vaporized feedstock;
b) a stage for heating said vaporized feedstock in an exchanger by means of a heat exchange with a thermal fluid, so as to produce a superheated feedstock having a temperature of greater than 400° C. and less than 550° C.;
c) a stage for dehydrating said superheated feedstock so as to produce a dehydration effluent, wherein said stage for dehydrating comprises a reaction section comprising at least one multitubular reactor in which the dehydration reaction takes place, said multitubular reactor comprising a plurality of tubes having a length of between 2 and 4 m and a shell, said tubes each comprising at least one fixed bed comprising at least one dehydration catalyst, said superheated feedstock being introduced into said tubes at an inlet temperature of greater than 400° C. and less than 550° C. and at an inlet pressure of between 0.8 and 1.8 MPa, a heat transfer fluid circulating inside said shell at a mass flow rate such that the ratio of the mass flow rate of said heat transfer fluid in the shell relative to the mass flow rate of said superheated feedstock introduced into said tubes is greater than or equal to 10, said heat transfer fluid having a temperature at the inlet into the shell of said multitubular reactor of greater than 430° C. and less than 550° C.;
d) a stage for separating the dehydration effluent resulting from stage c) into an effluent comprising ethylene at a pressure of less than 1 MPa and an effluent comprising water;
e) a stage for purifying at least a portion of the effluent comprising water resulting from stage d) and for separating at least one stream of purified water and at least one stream of unconverted ethanol.

The present invention has the advantage of achieving high ethanol conversion rates and high selectivity for ethylene while at the same time reducing the overall energy consumption of the process compared to the prior art processes. Specifically, the applicant has discovered, surprisingly, that the dehydration reaction of ethanol to give ethylene, which is a highly endothermic reaction, is possible in a multitubular reactor under particular operating conditions. Under such conditions, the temperatures necessary for good conversion of the ethanol to ethylene are achieved.

The present invention thus makes it possible to compensate for the endothermic nature of the dehydration reaction in order to ensure good conversion of the ethanol to ethylene while at the same time limiting side reactions and thus avoiding the production of byproducts (butenes, oligomers, aromatic compounds, etc.).

The present invention also enables a reduction in the temperature of the feedstock at the inlet of the multitubular reactor compared to those used at the inlet of the first adiabatic reactor of the prior art processes, thus limiting any risk of possible degradation of the feedstock.

The present invention also has the advantage of maximizing the heat exchange between the feedstock and the dehydration effluent resulting from the dehydration reactor, that is to say of exchanging all of the enthalpy of vaporization of the feedstock and the major portion of the enthalpy of condensation of said effluent.

DESCRIPTION OF THE INVENTION

The invention thus relates to a process for dehydrating an ethanol feedstock to give ethylene, comprising:

a) a stage for vaporizing a vaporization feedstock comprising said—optionally pretreated—ethanol feedstock in an exchanger by means of a heat exchange with a dehydration effluent resulting from stage c), so as to produce a vaporized feedstock;
b) a stage for heating said vaporized feedstock in an exchanger by means of a heat exchange with a thermal fluid, so as to produce a superheated feedstock having a temperature of greater than 400° C. and less than 550° C.;
c) a stage for dehydrating said superheated feedstock so as to produce a dehydration effluent, wherein said stage for dehydrating comprises a reaction section comprising at least one multitubular reactor in which the dehydration reaction takes place, said multitubular reactor comprising a plurality of tubes having a length of between 2 and 4 m and a shell, said tubes each comprising at least one fixed bed comprising at least one dehydration catalyst, preferably a zeolitic catalyst, said superheated feedstock being introduced into said tubes at an inlet temperature of greater than 400° C. and less than 550° C. and at an inlet pressure of between 0.8 and 1.8 MPa, a heat transfer fluid circulating inside said shell at a mass flow rate such that the ratio of the mass flow rate of said heat transfer fluid in the shell relative to the mass flow rate of said superheated feedstock introduced into said tubes is greater than or equal to 10, said heat transfer fluid having a temperature at the inlet into the shell of greater than 430° C. and less than 550° C.;
d) a stage for separating the dehydration effluent resulting from stage c) into an effluent comprising ethylene at a pressure of less than 1 MPa and an effluent comprising water;
e) a stage for purifying at least a portion of the effluent comprising water resulting from stage d) and for separating at least one stream of purified water and at least one stream of unconverted ethanol.

Feedstock

According to the invention, the feedstock treated in the dehydration process is an ethanol feedstock.

Said ethanol feedstock advantageously comprises ethanol. It may also comprise water. Said ethanol feedstock is advantageously a concentrated ethanol feedstock. The term "concentrated ethanol feedstock" is understood to mean an ethanol feedstock comprising a mass percentage of ethanol of greater than or equal to 35% by weight. Preferably, said concentrated ethanol feedstock comprises a mass percentage of ethanol of between 35% and 99.9% by weight.

The ethanol feedstock comprising less than 35% by weight of ethanol can be concentrated prior to the process of the invention by any means known to those skilled in the art, for example by distillation, by absorption, by pervaporation.

Said ethanol feedstock can also comprise, in addition to water, a content of alcohols other than ethanol, for instance methanol, butanol and/or isopentanol, of less than 10% by weight, and preferably less than 5% by weight, a content of oxygen-based compounds other than alcohols, for instance ethers, acids, ketones, aldehydes and/or esters, of less than 1% by weight, and a content of organic and inorganic nitrogen and sulfur of less than 0.5% by weight, the weight percentages being expressed relative to the total mass of said feedstock.

The ethanol feedstock treated in the process according to the invention is optionally obtained via an alcohol synthesis process proceeding from fossil resources, for instance proceeding from coal, natural gas or carbon-based waste.

Said feedstock may also advantageously originate from non-fossil resources. Preferably, the ethanol feedstock treated in the process according to the invention is an ethanol feedstock produced from a renewable source derived from biomass, often referred to as "bioethanol". Bioethanol is a feedstock produced biologically, preferably by fermentation of sugars obtained, for example, from sugar-yielding plant crops such as sugarcane (saccharose, glucose, fructose and sucrose), from beetroot, or from starchy plants (starch) or from lignocellulosic biomass or from hydrolyzed cellulose (predominantly glucose, and xylose and galactose), containing variable amounts of water.

For a more complete description of the conventional fermentation processes, reference may be made to the publication "Les Biocarburants, État des lieux, perspectives et enjeux du développement [Biofuels, current state, perspectives and development challenges]", Daniel Ballerini, published by Technip, 2006.

Said feedstock may also advantageously be obtained from synthesis gas.

Said feedstock may also advantageously also be obtained by hydrogenation of the corresponding acids or esters. In this case, acetic acid or acetic esters are advantageously hydrogenated using hydrogen to give ethanol. Acetic acid may advantageously be obtained by carbonylation of methanol or by fermentation of carbohydrates.

Preferably, the ethanol feedstock according to the invention is an ethanol feedstock produced from a renewable source derived from biomass.

The ethanol feedstock according to the invention may optionally advantageously undergo a stage of pretreatment prior to stage a) of vaporization of said feedstock. Said pretreatment stage makes it possible to remove the impurities contained in said feedstock so as to limit the deactivation of the dehydration catalyst placed downstream, and in particular compounds containing nitrogen and compounds containing sulfur. The oxygen-based compounds present in said feedstock are not substantially removed. It may also advantageously contribute to the reduction of the energy consumption of the dehydration process.

Said pretreatment stage is advantageously implemented by means known to those skilled in the art, such as for example: the use of at least one resin, preferably an acidic resin; the adsorption of the impurities onto solids preferably at a temperature of between 20 and 60° C.; a sequence comprising a first stage of hydrogenolysis operating at a temperature of between 20 and 80° C. followed by a stage of capture on acidic solid at a temperature of between 20 and 80° C.; and/or distillation. In the case of the use of at least one resin, said resin is preferably acidic and is used at an elevated temperature of between 70 and 200° C. Said resin may optionally be preceded by a basic resin. In the case where the pretreatment stage is implemented by the adsorption of the impurities on solids, said solids are advantageously selected from molecular sieves, activated carbon, alumina and zeolites.

In one particular embodiment of the invention, the stage of pretreatment of the ethanol feedstock prior to vaporization stage a) comprises a preheating of said ethanol feedstock followed by a pretreatment. Said preheating of said ethanol feedstock is implemented in a heat exchanger so as to produce a preheated ethanol feedstock, by means of an exchange of heat with the dehydration effluent resulting from stage c) in order to bring said feedstock to a temperature of between 100 and 130° C., the pressure being between 0.1 and 3 MPa such that said ethanol feedstock at the end of the preheating remains in liquid form. Said pretreatment of the preheated ethanol feedstock is implemented on an acidic solid, preferably having an exchange capacity of at least 0.1 mmol $H^+$ equivalent per gram, the exchange capacity (or acid strength) being determined by dosing (preferably by conductimetry) of the H+ ions released by the acidic solid after exchange with Na+ ions (See ASTM D4266). Preferably, said acidic solid is selected from the group consisting of acid-treated clays (such as montmorillonite), zeolites having a molar ratio of silica to alumina in the crystal lattice of 2.5 to 100 and acidic resins, in particular having an exchange capacity of 0.2 to 10 mmol H+ equivalent per gram. Preferably, the acidic solid used for the pretreatment of the ethanol feedstock in this embodiment is an ion exchange resin, in particular cation exchange resin, comprising in particular sulfonic groups grafted to an organic support composed of aromatic and/or haloaliphatic chains. Very preferentially, the acidic solid of the pretreatment of the ethanol feedstock optionally implemented prior to vaporization stage a) of the process of the present invention is an acidic resin comprising a copolymer of divinylbenzene and of polystyrene having a degree of crosslinking of between 20% and 45% and an acid strength (or exchange capacity) representing the number of active sites of said resin of between 1 and 10 mmol H+ equivalent per gram, preferably of between 3.5 and 6 mmol H+ equivalent per gram. For example, the acidic solid is a commercial acidic resin sold under the reference TA801 by Axens. This particular mode of pretreatment of said ethanol feedstock is well described, for example, in the patents FR 2 998 567 and FR 2 998 568.

In another particular embodiment of the invention, the stage of pretreatment of the ethanol feedstock prior to vaporization stage a) comprises a stage of capture on an adsorbent, preferably selected from the group formed by: microporous aluminosilicate materials, resins bearing acid groups, acidic ion exchange resins, acid-impregnated silicas, activated carbons, activated aluminas, clays, molecular sieves, mesoporous aluminosilicate materials and mixtures thereof. This stage of capture of the impurities on an adsorbent may be preceded by a stage of hydrogenation of the impurities of the ethanol feedstock, in particular the nitrile and/or aldehyde impurities, in the presence of hydrogen and of a hydrogenation catalyst such as a resin (for example a resin of Amberlyst® type), an FAU-type zeolite (for example a Y zeolite) or a silica-alumina material impregnated with an element Pd, Pt, Co, Mo or Ni. This other particular mode of pretreatment of said ethanol feedstock is well described, for example, in patent application WO 2010/060981.

Said stage of pretreatment of the ethanol feedstock makes it possible to produce a purified fraction of the ethanol feedstock in which the organic impurities have been removed, in order to obtain a purified feedstock meeting the level of impurities compatible with the dehydration catalyst. Said pretreatment stage may also make it possible to partially transform the ethanol into diethyl ether (DEE), for example between 3% by weight and 20% by weight of the ethanol present in the feedstock converted into DEE during this pretreatment stage.

Vaporization stage a)

According to the invention, the dehydration process comprises a stage a) for vaporizing a vaporization feedstock comprising said—optionally pretreated—ethanol feedstock, so as to produce a vaporized feedstock. Said vaporization is carried out by means of a heat exchange with the effluent resulting from dehydration stage c) in a heat exchanger.

Said—optionally pretreated—ethanol feedstock is advantageously mixed with at least a portion, preferably all, of a stream of unconverted ethanol resulting from purification stage e) which is recycled and introduced upstream of the exchanger of vaporization stage a).

Said—optionally pretreated—ethanol feedstock which is advantageously mixed with at least a portion, preferably all, of the recycled stream of unconverted ethanol is referred to in the continuation of the disclosure as "vaporization feedstock".

Advantageously, the pressure of said vaporization feedstock at the inlet of said vaporization stage a) is between 0.1 and 2.0 MPa, preferably between 0.1 and 1.4 MPa, preferentially between 0.8 and 1.3 MPa and very preferably between 1.0 and 1.2 MPa.

Over the course of vaporization stage a), the majority of the latent heat of the aqueous phase of the dehydration effluent resulting from the multitubular reactor is recovered for vaporizing said vaporization feedstock, without the supply of external heat. The entirety of the enthalpy of vaporization of said vaporization feedstock is therefore exchanged with the enthalpy of condensation of said dehydration effluent. During vaporization stage a), the vaporization feedstock evaporates and the dehydration effluent condenses at least partially. Advantageously, at the end of vaporization stage a), the vaporized feedstock is at least partially, preferably entirely, in gas form.

The specific operating conditions of vaporization stage a) also make it possible to avoid supplying heat transfer fluid external to the process for ensuring the vaporization of said vaporization feedstock by recovering the majority of the latent heat of the aqueous phase of the dehydration effluent resulting from the multitubular reactor for vaporizing the vaporization feedstock. Thus, only the streams resulting from the process are used.

The vaporization feedstock may also optionally be reheated, upstream of vaporization stage a) but after the optional mixing of the ethanol feedstock with the stream of unconverted ethanol which is recycled according to stage e), by heat exchange with the stream of unconverted ethanol resulting from separation stage e) or with the stream of purified water resulting from separation stage e), or by a succession of heat exchanges with the stream of unconverted ethanol resulting from stage e) and with the stream of purified water resulting from stage e). This prior heating stage, if it is integrated into the process according to the invention, is advantageously implemented in any suitable type of exchanger, preferably a liquid/liquid exchanger, known to those skilled in the art. This thermal integration makes it possible to maximize the recovery of heat from the effluents produced for heating the feedstock. It thus contributes to reducing the energy consumption of the process.

Heating stage b)

According to the invention, the dehydration process comprises a stage b) for heating said vaporized feedstock resulting from vaporization stage a), so as to produce a superheated feedstock.

Advantageously, the obtained superheated feedstock is in gas form. Advantageously, said vaporized feedstock is heated in an exchanger by means of a heat exchange with a thermal fluid.

This heating stage makes it possible to bring the vaporized feedstock, advantageously in gas form, to a temperature compatible with the temperature of the dehydration reaction of the ethanol. Preferably, the temperature of the superheated feedstock obtained at the end of stage b) of the process according to the invention is greater than 400° C., preferentially greater than or equal to 410° C., very preferably greater than or equal to 420° C., and less than 550° C., preferentially less than or equal to 500° C.

To achieve these elevated temperatures for the vaporized feedstock by heat exchange, the used thermal fluid should have a temperature at the inlet of the heat exchanger of greater than 430° C., preferably greater than or equal to 450° C., very preferably greater than or equal to 470° C., and less than 550° C., preferably less than or equal to 500° C., preferentially less than or equal to 495° C.

The thermal fluid is thus selected so as to be thermally stable under the operating conditions as described above, preferably at an operating temperature of greater than 430° C. Preferably, the thermal fluid is also chemically inert with respect to the compounds of the feedstock and does not induce corrosion in the equipment used in the process according to the invention, in particular in the exchanger of stage b).

Advantageously, the thermal fluid is selected from the group consisting of: molten salts (or heat transfer salts) and oils of high-performance lubricant type. Preferably, the thermal fluid is selected from molten salts. An oil of high-performance lubricant type which may be used as thermal fluid in the process according to the invention is for example the oil sold by Santolube under the name OS-124. Preferably, the thermal fluid is selected from the following molten salts: $NaNO_3$-KNOB mixtures, for example the $NaNO_3$-KNOB Solar Salt grades, $NaNO_3$—$NaNO_2$-KNOB eutectic mixtures, for example Dynalene MS-1 sold by Dynalene or Hitec® sold by Brenntag, and mixtures of the fluoride salts NaF and NaBF4. Preferably, the thermal fluid is selected from $NaNO_3$-$NaNO_2$-KNOB eutectic mixtures (for example known under the commercial names Dynalene MS-1 and Hitec®).

When molten salts are used as thermal fluid, they remain in liquid form at the operating temperatures of the process. The heat exchange is therefore preferably carried out in a liquid/gas type exchanger.

Very preferably, the thermal fluid used in heating stage b) of the process according to the invention is the same as the heat transfer fluid used in the multitubular reactor of dehydration stage c). Thus, a single external heat transfer fluid is introduced into the process, limiting the energy consumption and the costs linked to the consumption of utilities.

Advantageously, the process according to the invention comprises a closed thermal fluid circulation loop, preferably a single closed external heat transfer fluid circulation loop when the thermal fluid of stage b) and the heat transfer fluid of stage c) are the same. The closed thermal fluid circulation loop comprises a fluid heating system, such as for example a tubular oven. This circulation loop may also comprise collecting vessels for recovering the "wastes", compounds, especially liquid compounds, other than the molten salts or the high-performance oils chosen and originating from the exchanger of heating stage b) (and/or from the multitubular reactor of dehydration stage c) when the thermal fluid of stage b) and the heat transfer fluid of stage c) are the same).

Dehydration stage c)

According to the invention, the dehydration process comprises a stage c) for dehydrating said superheated feedstock, so as to produce a dehydration effluent. Said dehydration stage c) comprises a reaction section comprising at least one multitubular reactor in which the dehydration reaction takes place.

Dehydration stage c) is advantageously carried out in a multitubular reactor.

Advantageously, said multitubular reactor comprises a plurality of tubes and a shell. The shell, which is typically cylindrical, is the envelope of the reactor inside which the tubes are located, preferably parallel to one another and to the walls of the shell, and a heat transfer fluid circulates. The shell can also comprise one or more baffles or any other system, distributed preferably uniformly in the shell, in order to permit good diffusion and homogenization of the heat transfer fluid. According to the invention, the tubes each comprise at least one fixed bed comprising at least one dehydration catalyst. The dehydration reaction takes place in the tubes of the multitubular reactor(s). In the continuation of the disclosure, the tubes of the multitubular reactor, each comprising at least one fixed bed comprising at least one dehydration catalyst, may also be referred to as reaction tubes.

Advantageously, the multitubular reactor of stage c) comprises a plurality of tubes in the shell, preferably at least 100 tubes, preferentially at least 1000 tubes, or even at least 2000 tubes. Generally, multitubular reactors comprise up to 10 000 tubes.

According to the invention, the reaction tubes have a length of between 2 and 4 m, preferably between 2.5 and 3.5 m. The external diameter of the reaction tubes is typically between 10 and 80 mm, preferably between 20 and 75 mm and preferentially between 40 and 60 mm, for example approximately 2 inches, and their internal diameter is preferably between 9 and 79 mm, preferentially between 15 and 70 mm and very preferably between 35 and 55 mm.

The size of the multitubular reactor of dehydration stage c), such as the diameter of the shell, can be adapted by those skilled in the art in accordance with general knowledge, depending in particular on the number of tubes, their length and their diameter.

Multitubular reactors, especially industrial multitubular reactors, are conventionally made of a material which is inert with respect to the reaction which is carried out, typically made of stainless steel, steel or nickel. The multitubular reactor(s) in the process according to the invention is/are preferably made of stainless steel.

According to the invention, said superheated feedstock is introduced into said tubes of the multitubular reactor, each comprising at least one fixed bed comprising at least one dehydration catalyst, advantageously at one of the ends of said reaction tubes and simultaneously into all of the reaction tubes of said multitubular reactor. Advantageously, the temperature of said superheated feedstock at the inlet into said reaction tubes is greater than 400° C., preferably greater than or equal to 410° C., very preferably greater than or equal to 420° C., and less than 550° C., preferably less than or equal to 500° C., preferentially less than or equal to 480° C. and very preferably less than or equal to 450° C. The pressure of said superheated feedstock at the inlet into said reaction tubes is advantageously between 0.8 and 1.8 MPa, preferably between 0.8 and 1.1 MPa, preferentially between 0.85 and 1.0 MPa and very preferably between 0.90 and 0.95 MPa.

The dehydration effluent resulting from said multitubular reactor of stage c) advantageously has a temperature of between 340 and 500° C., preferably between 380 and 450° C., preferentially between 400 and 450° C., and a pressure at the reactor outlet of between 0.6 and 1.6 MPa and preferably between 0.6 and 0.8 MPa.

The temperature of said superheated feedstock at the inlet into the reactor(s) may advantageously be increased gradually, advantageously within the range of inlet temperatures noted above, in order to adapt to the deactivation of the dehydration catalyst.

The dehydration reaction which takes place in at least one multitubular reactor of stage c) of the process according to the invention advantageously operates at a weight hourly space velocity (WWH) of between 0.1 and 20 $h^{-1}$ and preferably between 0.5 and 15 $h^{-1}$. The weight hourly space velocity (WWH, weight per weight per hour) is defined as being the ratio of the mass flow rate of the feedstock entering the reactor, i.e. the superheated feedstock, to the mass of dehydration catalyst present in all of the reaction tubes of said multitubular reactor.

The flow of the feedstock may be in upflow or downflow mode, preferably downflow mode.

Advantageously, a heat transfer fluid circulates in the shell, in particular between said reaction tubes, of the multitubular reactor(s) of said dehydration stage c), in cocurrent with or countercurrent to the flow circulating within the reaction tubes. The mass flow rate of said heat transfer fluid in the shell is such that the ratio of the mass flow rate of said heat transfer fluid in the shell relative to the mass flow rate of said superheated feedstock introduced into said tubes is greater than or equal to 10, preferably between 11 and 15, preferentially between 12 and 14.

A heat transfer fluid is used in the process according to the invention to supply the heat necessary for the dehydration reaction which takes place in the tubes. There is therefore heat exchange in the wall by transfer of sensible heat. Since the dehydration reaction of ethanol to give ethylene is highly endothermic, fairly high (in particular 380-450° C.) attack temperatures are necessary in the reaction tubes (i.e. in the tubes zone located at the inlet of the feedstock). In order to have a good temperature gradient between the reaction feedstock (inside the tubes) and the heat transfer fluid (inside the shell) and in order to achieve a good conversion of the ethanol, the temperature of the heat transfer fluid at the inlet of the multitubular reactor should be greater than the temperature of the feedstock at the inlet into the tubes. Thus, the temperature of said heat transfer fluid at the inlet into the shell of said multitubular reactor is advantageously greater than 430° C., preferably greater than or equal to 450° C., very preferably greater than or equal to 470° C., and less than 550° C., preferably less than or equal to 500° C., preferentially less than or equal to 495° C.

The heat transfer fluid is chosen so as to be thermally stable under the operating conditions as described above, in particular at an operating temperature of greater than 430° C. The choice of heat transfer fluid may also be guided by other constraints: the heat transfer fluid is inert with respect to the reactants and the products of the dehydration reaction; the heat transfer fluid does not induce corrosion of the equipment of the process according to the invention, such as the multitubular reactor or the pipes.

Advantageously, the heat transfer fluid is selected from the group consisting of: molten salts (or heat transfer salts) and oils of high-performance lubricant type. For example, an oil of high-performance lubricant type which may be used as heat transfer fluid in the process according to the invention is the oil sold by Santolube under the name OS-124. Preferably, the heat transfer fluid is selected from molten salts which are in liquid form at the operating temperatures of the multitubular reactor of the process according to the invention. Very preferably, the heat transfer fluid is selected from the following molten salts: $NaNO_3$—$KNO_3$ mixtures, for example the $NaNO_3$—$KNO_3$ Solar Salt grades, $NaNO_3$—$NaNO_2$—$KNO_3$ eutectic mixtures (molten salts of Hitec® type), for example the commercial Hitec® grades sold by Brenntag or Dynalene MS-1 sold by Dynalene under the name, and mixtures of fluoride salts NaF and $NaBF_4$.

Preferably, the heat transfer fluid is selected from NaNO$_3$—NaNO$_2$—KNO$_3$ eutectic mixtures (for example Dynalene MS-1).

Very preferably, the heat transfer fluid used in the multitubular reactor of dehydration stage c) is the same as the thermal fluid used in heating stage b).

Advantageously, the process according to the invention comprises a closed heat transfer fluid circulation loop, preferably a single closed external heat transfer fluid circulation loop when the thermal and heat transfer fluids are the same. The closed heat transfer fluid circulation loop comprises a fluid heating system, such as for example a tubular oven. This circulation loop may also comprise collecting vessels for recovering the "wastes", compounds, especially liquid compounds, other than the molten salts or the high-performance oils chosen and originating from the multitubular reactor of dehydration stage c) (and/or from the exchanger of heating stage b) when the thermal fluid of stage b) and the heat transfer fluid of stage c) are the same).

In such a reactor and with the particular operating conditions in particular of stages b) and c) of the process according to the invention, the dehydration reaction of ethanol to give ethylene proceeds under isothermal or pseudo-isothermal conditions, that is to say that the temperature of the reaction medium at the reactor outlet (i.e. of the dehydration effluent at the reactor outlet) is similar to the inlet temperature of the feedstock or exhibits a difference of less than 40° C., preferably less than 20° C., with respect to the temperature of the feedstock at the reactor inlet. These particular operating conditions contribute to obtain high conversion rates of the ethanol with a high selectivity for ethylene, while at the same time having satisfactory energy consumption, or even reduced energy consumption compared to a process comprising a series of adiabatic reactors.

The dehydration catalyst used in dehydration stage c) is a catalyst known to those skilled in the art. Preferably, said catalyst is an amorphous acid catalyst or a zeolitic catalyst. Very preferably, the dehydration catalyst used in stage c) of the process according to the invention is an, in particular acid, zeolitic catalyst.

In the case where the dehydration catalyst used in stage c) is a zeolitic catalyst, said catalyst comprises at least one zeolite selected from zeolites having at least pore apertures containing 8, 10 or 12 oxygen atoms (8 MR, 10 MR or 12 MR). Specifically, it is known to define the size of the pores of zeolites by the number of oxygen atoms forming the ring section of the channels of the zeolites, referred to as "member ring" or MR. Preferably, said zeolitic dehydration catalyst comprises at least one zeolite having a structural type selected from the MFI, FAU, MOR, FER, SAPO, TON, CHA, EUO MEL and BEA structural types. Preferably, said zeolitic dehydration catalyst comprises a zeolite of MFI structural type and preferably a ZSM-5 zeolite.

The zeolite employed in the dehydration catalyst used in stage c) of the process according to the invention may advantageously be modified by dealumination or desilication according to any dealumination or desilication method known to those skilled in the art.

The zeolite employed in the dehydration catalyst used in stage c) of the process according to the invention or the final catalyst may advantageously be modified by an agent having the property of weakening its overall acidity and improving its hydrothermal resistance properties. Preferably, said zeolite or said catalyst advantageously comprises phosphorus, preferably added in the form of H$_3$PO$_4$ followed by steam treatment after neutralization of the excess acid with a basic precursor for example based on sodium Na or calcium Ca.

Preferably, said zeolite comprises a phosphorus content of between 1% and 4.5% by weight, preferably between 1.5% and 3.1% by weight, relative to the total weight of the catalyst.

Preferably, the dehydration catalyst used in stage c) of the process according to the invention is the catalyst described in patent applications WO 2009/098262, WO 2009/098267, WO 2009/098268 or WO 2009/098269. Very preferably, the dehydration catalyst used in stage c) of the process according to the invention comprises a zeolite of MFI structural type, preferably a ZSM-5 zeolite, and phosphorus at a content of between 1% and 4.5% by weight, preferably between 1.5% and 3.1% by weight, relative to the total weight of the catalyst.

In the preferred case where the dehydration catalyst used in stage c) is a zeolitic catalyst, the ethanol feedstock is preferably pretreated upstream of vaporization stage a). The pretreatment stage thus advantageously makes it possible to remove the impurities contained in said ethanol feedstock which are "inhibitors" of the dehydration catalyst, so as to limit, or rather delay, the deactivation of said catalyst.

In the case where the dehydration catalyst used in stage c) of the process according to the invention is an amorphous acid catalyst, said catalyst comprises at least one porous refractory oxide selected from alumina, alumina activated by deposition of a mineral acid, and silica-alumina.

Said dehydration catalyst used in stage c) of the process according to the invention, preferably comprising a zeolite, may advantageously also comprise at least one matrix of oxide type, also referred to as binder. According to the invention, the term "matrix" is understood to mean an amorphous or crystallized matrix or one comprising amorphous and crystallized portions. Said matrix is advantageously selected from the elements of the group formed by clays (such as for example from natural clays such as kaolin or bentonite), magnesia, aluminas, silicas, silica-aluminas, aluminates, titanium oxide, boron oxide, zirconia, aluminum phosphates, titanium phosphates, zirconium phosphates and charcoal, used alone or as a mixture. Preferably, said matrix is selected from the elements of the group formed by aluminas, silicas and clays.

Said dehydration catalyst used in stage c) of the process according to the invention is advantageously shaped into the form of grains of various shapes and sizes. It is advantageously used in the form of cylindrical extrudates or polylobal extrudates such as bilobal, trilobal or polylobal extrudates of straight or twisted form, but may optionally be manufactured and employed in the form of crushed powder, lozenges, rings, beads, wheels or spheres. Preferably, said catalyst is in the form of extrudates.

Stage c) of the process according to the invention, in particular in the presence of the dehydration catalyst, preferably comprising a zeolite, contained in the specific reactor and under the operating conditions used, makes it possible to optimize the conversion of the ethanol and the selectivity for ethylene, by compensating for the loss of heat due to the endothermic nature of the dehydration reaction without inducing side reactions. Stage c) of the process of the invention thus makes it possible to maximize the production of ethylene while at the same time limiting the formation of byproducts such as butenes, oligomers and aromatic compounds. The overall dehydration reaction implemented in stage c) of the process according to the invention is as follows:

$$2C_2H_5OH \rightarrow 2CH_2=CH_2 + 2H_2O$$

The conversion of the ethanol feedstock in stage c) is greater than 90%, preferably 95% and with preference greater than 99%. The conversion of the ethanol feedstock is defined, as a percentage, by the following formula:

[1—(hourly mass of ethanol at the outlet/hourly mass of ethanol at the inlet)]×100.

The hourly mass of ethanol at the inlet and at the outlet is the hourly mass at the inlet and at the outlet of the multitubular reactor, measured in a conventional manner for example by gas chromatography.

During stage c) of the process according to the invention, the transformation of the feedstock may be accompanied by the deactivation of the dehydration catalyst by coking and/or by adsorption of inhibitor compounds. The dehydration catalyst, preferably the catalyst comprising a zeolite, thus advantageously periodically undergoes a stage of regeneration. Preferably, the reactor is used in an alternating regeneration mode, also referred to as a swing reactor, in order to alternate the reaction and regeneration phases of said dehydration catalyst. The objective of this regeneration treatment is to burn the organic deposits and also the species containing nitrogen and sulfur present at the surface and within said dehydration catalyst. The optional pretreatment of the ethanol feedstock makes it possible to reduce the amount of impurities, basic and organic, as well as the cationic species which will alter the cycle time of the catalyst. The removal of these species thus makes it possible to limit the number of regenerations of the catalyst.

The regeneration of the dehydration catalyst used in said stage c) of the process according to the invention is advantageously carried out by oxidation of the coke and of the inhibitor compounds under a stream of air or under an air/nitrogen mixture, for example by using recirculation of the combustion air with or without water in order to dilute the oxygen and control the regeneration exothermicity. In this case, the content of oxygen at the inlet of the reactor may advantageously be adjusted by a supplement of air. The regeneration takes place at a pressure between atmospheric pressure and the reaction pressure.

The regeneration temperature is advantageously selected to be between 400 and 600° C.; it may advantageously vary during regeneration. The end of the regeneration is detected when there is no more consumption of oxygen, which is a sign of complete combustion of the coke.

The dehydration effluent resulting from the multitubular reactor of stage c) is advantageously sent to a gas/liquid type exchanger in which it is partially condensed by a heat exchange serving to vaporize the vaporization feedstock in vaporization stage a).

Said dehydration effluent may then be cooled further by heat exchange with the ethanol feedstock during the optional preheating phase which may advantageously precede the optional pretreatment of the ethanol feedstock upstream of vaporization stage a).

Separation stage d)

According to the invention, the dehydration effluent resulting from stage c) undergoes a separation stage d) into an effluent comprising ethylene at a pressure of less than 1 MPa, preferentially of less than 0.8 MPa, and an effluent comprising water.

Stage d) for separating said dehydration effluent resulting from stage c) may advantageously be implemented by any method known to those skilled in the art, such as for example by a gas/liquid separation zone, and preferably a gas/liquid separation column.

The effluent comprising ethylene at a pressure of less than 1 MPa then advantageously undergoes compression. Said compression makes it possible to raise the pressure of said effluent to a pressure advantageously of between 2 and 4 MPa, necessary for its final purification.

At least a portion of the effluent comprising water resulting from stage d) is optionally recycled into separation stage d). This recycling makes it possible to increase the efficiency of stage d) by absorbing a portion of the unconverted feedstock. In the case where at least a portion of the effluent comprising water is recycled, said portion of the effluent comprising water is advantageously cooled with the aid of a cold fluid or a fluid resulting from the process and is preferably treated according to the known purification methods described below.

Purification stage e)

According to the invention, at least a portion of the effluent comprising water resulting from separation stage d) undergoes a stage e) of purification. Purification stage e) may advantageously be implemented by any purification method known to those skilled in the art. By way of example, purification stage e) may advantageously be implemented by the use of ion exchange resins, by addition of chemical agents for adjusting the pH such as for example sodium hydroxide or amines and/or by addition of chemical agents for stabilizing the products, such as for example polymerization inhibitors selected from bisulfites and surfactants.

At least one stream of purified water and at least one stream of unconverted ethanol are then separated.

The separation may advantageously be implemented by any separation method known to those skilled in the art. By way of example, the separation may advantageously be implemented by distillation, the use of molecular sieves, steam or heat stripping or by absorption in a solvent such as for example glycol solvents.

A stream containing the light gases, preferably acetaldehyde and methanol, may advantageously also be separated.

According to the invention, at least a portion, preferably all, of the stream of unconverted ethanol resulting from stage e) may be recycled upstream of vaporization stage a). The recycled stream of unconverted ethanol resulting from stage e) is mixed with the—optionally pretreated—ethanol feedstock.

This stage of recycling of at least a portion of the stream of unconverted ethanol, when it is integrated in the process according to the invention, makes it possible to improve ethylene yields.

BRIEF DESCRIPTION OF THE DRAWINGS

FIG. 1 schematically represents the dehydration process according to the invention in the case of the dehydration of a concentrated ethanol feedstock with a stage of pretreatment of the ethanol feedstock, a recycling of at least a portion of the stream of unconverted ethanol upstream of vaporization stage a) and a complete thermal integration of the streams resulting from the purification. In this embodiment, the thermal fluid of the heating stage and the heat transfer fluid of the dehydration stage are the same fluid.

The ethanol feedstock is introduced into a pretreatment zone (2) via the pipe (1). The pretreated ethanol feedstock (3) is then mixed in the pipe (5) with a portion of the stream of unconverted ethanol (4) resulting from the purification zone (15) and recycled via the pipe (4). The pretreated ethanol feedstock as a mixture with a recycled portion of the stream of unconverted ethanol is introduced via the pipe (5)

into an exchanger E1 in which said mixture undergoes an exchange of heat with the stream of unconverted ethanol (16) resulting from the purification zone (15). Said mixture is then introduced via the pipe (6) into a second exchanger E2 in which it undergoes an exchange of heat with the stream of purified water (17) resulting from the purification zone (15).

Said mixture comprising the pretreated ethanol feedstock and a recycled portion of the stream of unconverted ethanol, preheated in the exchangers E1 and E2, is then sent via the pipe (7) into an exchanger E3 in which it undergoes an exchange of heat with the dehydration effluent resulting from the multitubular reactor R1. Said dehydration effluent is introduced into the exchanger E3 via the pipe (10) and leaves said exchanger via the pipe (11). The latent heat or enthalpy of condensation of the dehydration effluent resulting from the multitubular reactor R1 is used to vaporize the ethanol feedstock mixed with the recycled stream of unconverted ethanol, without the supply of external heat. A vaporized feedstock (8) is obtained at the outlet of the exchanger E3.

The vaporized feedstock is sent via the pipe (8) to a gas/liquid exchanger E4 in which said vaporized feedstock undergoes an exchange of heat with a heat transfer fluid (32), for example molten salts. A superheated feedstock (9), in gas form, at a temperature compatible with the temperature of the dehydration reaction is obtained at the outlet of exchanger E4.

The superheated feedstock is then introduced via the pipe (9) into the multitubular reactor Rl. The heat transfer fluid circulates in the shell of the reactor R1 into which it is introduced via the pipe (33) and exits the reactor R1 via the pipe (35). The heat transfer fluid at the inlet of the exchanger E4 and of the reactor R1, that is to say in the pipes (31), (32) and (33), is at a temperature greater than that of the temperature of the feedstock at the inlet into the multitubular reactor Rl. At the outlet of the exchanger E4 and of the reactor R1, the heat transfer fluid is then sent via the pipe (36) to an oven (30), for example a tubular oven, where it will be reheated. The reheated heat transfer fluid (31) is then returned to the exchanger E4 and the multitubular reactor R1 via the respective pipes (32) and (33).

The dehydration effluent resulting from the reactor R1 then undergoes an exchange of heat described above in the exchanger E3 into which it is introduced via the pipe (10). At the outlet of the exchanger E3, the dehydration effluent is sent via the pipe (11) to a gas/liquid separation column (12) where it is separated into an effluent comprising ethylene (13) and an effluent comprising water (14). A portion of the effluent comprising water is recycled after cooling into the column (12) via the pipe (20). The portion of the effluent comprising water which is not recycled into the column (12) is sent via the pipe (14) to a purification and separation stage (15). At the outlet of the purification and separation stage (15), at least one stream of purified water (17) and at least one stream of unconverted ethanol (16) are then obtained. A stream containing the light gases (19) is also separated and recycled to the gas/liquid separation column (12). After heat exchange in the exchangers E2 and El respectively, the stream of purified water (18) is recovered.

The following examples illustrate the invention without limiting the scope thereof.

EXAMPLES

Example 1

In Accordance with the Invention

Example 1 illustrates a process according to the invention.
The ethanol feedstock under consideration is produced by the fermentation of wheat, without extraction of gluten, by a process of dry milling type.
The composition of the ethanol feedstock is given in table 1, column 1.
The ethanol feedstock is pretreated on a TA801 type pretreatment resin at a temperature of 120° C. and a pressure of 1.15 MPa. At the end of this pretreatment, the amount of nitrogen-based compounds is reduced (See table 1).

Vaporization stage a)
Said ethanol feedstock is mixed with the recycled stream of unconverted ethanol resulting from purification stage e), the composition of which is given in table 1, column 3. The vaporization feedstock is then obtained: its composition and its mass flow rate are given in table 1, column 4.

TABLE 1

Mass compositions and mass flow rates of the different streams of the process

| composition (% by mass) | ethanol feedstock | pretreated ethanol feedstock | recycled stream of unconverted EtOH | Vaporization feedstock | Effluent at reactor outlet | Effluent comprising ethylene | Purified water |
|---|---|---|---|---|---|---|---|
| Ethanol | 93.0 | 87.6 | 8.8 | 87.0 | 0.7 | 0.2 | 0.0 |
| Water | 6.7 | 7.7 | 88.7 | 12.5 | 46.1 | 0.9 | 99.8 |
| ethylene | 0.0 | 0.0 | 0.0 | 0.0 | 51.5 | 96.1 | 0.0 |
| aliphatic compounds | 0.0 | 0.0 | 0.0 | 0.0 | 0.1 | 0.3 | 0.0 |
| oxygen-based compounds other than ethanol | 0.3 | 4.5 | 2.5 | 0.5 | 0.9 | 1.1 | 0.2 |
| Olefins other than ethylene | 0.0 | 0.0 | 0.0 | 0.0 | 0.7 | 1.5 | 0.0 |
| Nitrogen-based compounds | 0.005 | 0.000 | 0.000 | 0.000 | 0.000 | 0.000 | 0.000 |
| Total flow rate (kg/h) | 46 870 | 46 870 | 3594 | 50 465 | 50 458 | 27 007 | 19 857 |

The vaporization feedstock is introduced into an exchanger at a pressure of 1.03 MPa and is vaporized by exchange of heat with the dehydration effluent resulting from the multitubular reactor. At the exchanger outlet, a vaporized feedstock is obtained in gas form.

Heating stage b)

The vaporized feedstock is introduced into a gas/liquid exchanger. The heat transfer fluid used is Dynalene MS-1 ($NaNO_3$—$NaNO_2$—$KNO_3$ eutectic mixture) sold by Dynalene, at a temperature of 470° C. At the exchanger outlet, the superheated feedstock is at 420° C.

Dehydration stage c)

The superheated feedstock is then introduced into a multitubular reactor comprising 2283 tubes and a shell in which the Dynalene MS-1 used in the previous stage circulates. The characteristics of the multitubular reactor are described in table 2.

The multitubular reactor comprises a dehydration catalyst placed in the tubes of the multitubular reactor, said catalyst comprising 80% by weight of ZSM-5 zeolite treated with $H_3PO_4$ such that the content of $P_2O_5$ is 3.5% by weight.

TABLE 2

Characteristics of the multitubular reactor and of the dehydration stage

| Parameters | |
|---|---|
| Number of tubes | 2283 |
| Height of the tubes (m) | 3 |
| Outside diameter of the tubes (mm) | 50.8 |
| Inside diameter of the tubes (mm) | 45.3 |
| Inlet temperature of the feedstock (° C.) | 420 |
| Inlet pressure of the feedstock (MPa) | 0.91 |
| Inlet temperature of the molten salts (° C.) | 470 |
| Flow rate of the feedstock in the reactor (kg/h) | 50 465 |
| Flow rate of the molten salts in the reactor (t/h) | 639.1 |
| Ratio of the molten salt/feedstock mass flow rates | About 12.7 |
| WWH* ($h^{-1}$) | 7 |
| Temperature of the effluent at the reactor outlet (° C.) | 408 |
| Pressure of the effluent at the reactor outlet (MPa) | 0.71 |

*WWH (weight per weight per hour), being the weight hourly space velocity, is defined as being the ratio of the mass flow rate of the feedstock entering the reactor, i.e. in this case (mass flow rate of the ethanol feedstock + mass flow rate of the recycled stream of unconverted ethanol), to the mass of dehydration catalyst present in the multitubular reactor.

The effluent obtained at the reactor outlet, or dehydration effluent, is analyzed by gas chromatography. Its composition is given in table 1, column 5.

The rate of conversion of the ethanol at the reactor outlet is very satisfying: it is 99.1%. It is calculated as follows:

[1(hourly mass of EtOH at the reactor outlet/hourly mass of EtOH at the reactor inlet)]100.

The selectivity of the process for ethylene is approximately 98%. It is calculated as follows: (amount of ethylene contained in the effluent comprising ethylene)/(0.61× amount of converted ethanol), wherein the amount of converted ethanol is the amount of ethanol contained in the vaporization feedstock subtracted from the amount of ethanol contained in the unconverted ethanol effluent ; 0.61 g is the maximum amount of ethylene obtained by dehydrating 1 g of pure ethanol.

Separation stage d)

The effluent resulting from the multitubular reactor of stage c) then undergoes a heat exchange with the vaporization feedstock, as described above, and is sent to a gas/liquid separation column. An effluent comprising ethylene at a pressure equal to 0.60 MPa is separated, as is an effluent comprising water. This separation is carried out by the use of a gas/liquid separation column, with recycling of the water produced at the bottom of the column to the top of the column and after cooling and injection of a neutralizing agent.

The effluent comprising ethylene then undergoes compression to increase its pressure to 2.78 MPa before its final purification.

Purification stage e)

A stream of purified water and a stream of unconverted ethanol as well as a stream containing the light gases are then separated by conventional low-pressure distillation of the effluent comprising water resulting from separation stage d).

The separated stream of unconverted ethanol is reintroduced in its entirety as a mixture with the ethanol feedstock upstream of vaporization stage a).

The equivalent primary energy consumption, or specific consumption of the process, is 6 GJ equivalent per ton of ethylene produced.

Example 2

In Accordance with the Invention

Example 2 illustrates a process according to the invention. In example 2, the same dehydration catalyst as that of example 1 (80% by weight of ZSM-5 zeolite treated with $H_3PO_4$ such that the content of $P_2O_5$ is 3.5% by weight) is used, but it is at the end of the cycle.

The same ethanol feedstock as in example 1 is used. It is pretreated as described in example 1 (on TA801 resin at 120° C. and 1.15 MPa).

The characteristics of the multitubular reactor are identical to those of the reactor of example 1.

The same heat transfer fluid as in example 1 is used (Dynalene MS-1).

Only the physical characteristics of the feedstock and of the molten salts at the inlet of the multitubular reactor and of the dehydration effluent vary compared to those of example 1:

inlet temperature of the feedstock: 430° C.;
inlet pressure of the feedstock: 0.92 MPa;
flow rate of the feedstock: 50 465 kg/h;
inlet temperature of the molten salts: 495° C.;
flow rate of the molten salts: 639.1 t/h;
temperature of the effluent at the reactor outlet: 432° C.;
pressure of the effluent at the reactor outlet: 0.7 MPa.

The rate of conversion of the ethanol at the reactor outlet, calculated in the same way as in example 1, is 99.8%.

The selectivity of the process for ethylene, calculated in the same way as in example 1, is 99.9%.

The equivalent primary energy consumption, or specific consumption of the process, is 5.72 GJ equivalent per ton of ethylene produced.

Example 3

Not In Accordance with the Invention

Example 3 illustrates a process for converting ethanol into ethylene, for example described in patent application WO 2013/011208.

The ethanol feedstock under consideration is the same as that of example 1. It is pretreated as described in example 1.

The process illustrated in example 3 comprises:

i) a stage of pretreatment of the ethanol feedstock on TA801 resin at 120° C., at 1.15 MPa.

ii) a stage for mixing the pretreated ethanol feedstock with a recycled portion of the stream of purified water and with the stream of unconverted ethanol which result from purification stage v), to obtain a vaporization feedstock comprising 65% by weight of water and 35% by weight of ethanol;

iii) a stage for vaporizing the obtained vaporization feedstock, by heat exchange with the dehydration effluent resulting from stage iii);

iv) a stage of compression of the vaporized feedstock;

v) a stage for dehydring the compressed vaporized feedstock, implemented in a succession of two adiabatic reactors, each comprising a fixed bed comprising a dehydration catalyst (the same catalyst as that of example 1), each of the adiabatic reactors being preceded by an oven for heating the reaction medium to temperatures compatible with the dehydration reaction: the feedstock is heated to a temperature at the inlet into the first adiabatic reactor of 460-480° C.; at the outlet of the first adiabatic reactor, the exiting effluent has lost 107° C. and is reheated in a second oven to 430-450° C. before entering the second adiabatic reactor;

vi) a stage of separation in a "quench" column of an effluent comprising ethylene and of an effluent comprising water;

vii) a stage of purification of the effluent comprising water and separation of at least one stream of purified water and one stream of unconverted ethanol.

The overall rate of ethanol conversion, at the outlet of the second adiabatic reactor, is equal to 99.2%. The selectivity for ethylene in the process of example 3 is 97.8%. The overall rate of conversion and selectivity for ethylene are calculated in the same way as in example 1.

The energy index of the process of example 3, not in accordance with the invention, is high: the primary energy consumption of the process of example 3 is at least 7.3 GJ per ton of ethylene.

The invention claimed is:

1. A process for dehydrating an ethanol feedstock to give ethylene, comprising:
    a) a stage for vaporizing a vaporization feedstock comprising said ethanol feedstock in an exchanger by means of a heat exchange with a dehydration effluent resulting from stage c), so as to produce a vaporized feedstock;
    b) a stage for heating said vaporized feedstock in an exchanger by means of a heat exchange with a thermal fluid, so as to produce a superheated feedstock having a temperature of greater than 400° C. and less than 550° C.;
    c) a stage for dehydrating said superheated feedstock so as to produce a dehydration effluent, wherein said stage for dehydrating comprises a reaction section comprising at least one multitubular reactor in which the dehydration reaction takes place, said multitubular reactor comprising a plurality of tubes having a length of between 2 and 4 m and a shell, said tubes each comprising at least one fixed bed comprising at least one dehydration catalyst, said superheated feedstock being introduced into said tubes at an inlet temperature of greater than 400° C. and less than 550° C. and at an inlet pressure of between 0.8 and 1.8 MPa,
    a heat transfer fluid circulating inside said shell at a mass flow rate such that the ratio of the mass flow rate of said heat transfer fluid in the shell relative to the mass flow rate of said superheated feedstock introduced into said tubes is greater than or equal to 10, said heat transfer fluid having a temperature at the inlet into the shell of said multitubular reactor of greater than 430° C. and less than 550° C.;
    d) a stage for separating the dehydration effluent resulting from stage c) into an effluent comprising ethylene at a pressure of less than 1 MPa and an effluent comprising water; and
    e) a stage for purifying at least a portion of the effluent comprising water resulting from stage d) and the separation of at least one stream of purified water and at least one stream of unconverted ethanol.

2. The process as claimed in claim 1, wherein said dehydration catalyst used in stage c) is a zeolitic catalyst comprising at least one zeolite selected from zeolites having an MFI structural type.

3. The process as claimed in claim 1, wherein said ethanol feedstock additionally undergoes a stage of pretreatment prior to vaporization stage a).

4. The process as claimed in claim 1, wherein at least a portion
    of the stream of unconverted ethanol resulting from stage e) is recycled and introduced upstream of the exchanger of vaporization stage a).

5. The process as claimed in claim 1, wherein the pressure of said vaporization feedstock at the inlet of said vaporization stage a) is between 0.1 and 2.0 MPa.

6. The process as claimed in claim 1, wherein said thermal fluid of said stage b) is selected from the molten salts: $NaNO_3$-$KNO_3$ mixtures, $NaNO_3$-$NaNO_2$-$KNO_3$ eutectic mixtures, and mixtures of the fluoride salts NaF and $NaBF_4$.

7. The process as claimed in claim 1, wherein the length of the tubes of said multitubular reactor of dehydration stage c) is between 2.5 and 3.5 m.

8. The process as claimed in claim 1, wherein the temperature of said superheated feedstock at the inlet into the multitubular reactor is greater than or equal to 410° C.

9. The process as claimed in claim 1, wherein the temperature of said superheated feedstock at the inlet into the multitubular reactor is less than or equal to 500° C.

10. The process as claimed in claim 1, wherein the pressure of said superheated feedstock at the inlet into the multitubular reactor is between 0.8 and 1.1 MPa.

11. The process as claimed in claim 1, wherein the heat transfer fluid of said stage c) is selected from the group consisting of: molten salts and oils of the high-performance lubricant type.

12. The process as claimed in claim 11, wherein said heat transfer fluid is selected from the molten salts: $NaNO_3$-$KNO_3$ mixtures, $NaNO_3$-$NaNO_2$-$KNO_3$ eutectic mixtures, and mixtures of the fluoride salts NaF and $NaBF_4$.

13. The process as claimed in claim 1, wherein said thermal fluid used in heating stage b) is the same as the heat transfer fluid used in the multitubular reactor of dehydration stage c).

14. The process as claimed in claim 1, wherein the temperature of said heat transfer fluid at the inlet into the shell of said multitubular reactor is greater than or equal to 450° C.

15. The process as claimed in claim 1, wherein the temperature of said heat transfer fluid at the inlet into the shell of said multitubular reactor is less than or equal to 500° C.

16. The process as claimed in claim 1, wherein the ratio of the mass flow rate of said heat transfer fluid in the shell relative to the mass flow rate of said superheated feedstock introduced into said tubes is between 11 and 15.

17. The process as claimed in claim 1, wherein said ethanol feedstock is an ethanol feedstock produced from a renewable source derived from biomass.

18. The process as claimed in claim 1, wherein the pressure of said vaporization feedstock at the inlet of said vaporization stage a) is between 1.0 and 1.2 MPa.

19. The process as claimed in claim 1, wherein said thermal fluid of said stage b) is selected from $NaNO_3$-$NaNO_2$-$KNO_3$ eutectic mixtures.

20. The process as claimed in claim 1, wherein the temperature of said superheated feedstock at the inlet into the multitubular reactor is greater than or equal to 420° C.

21. The process as claimed in claim 1, wherein the temperature of said superheated feedstock at the inlet into the multitubular reactor is less than or equal to 450° C.

22. The process as claimed in claim 1, wherein the pressure of said superheated feedstock at the inlet into the multitubular reactor is between 0.90 and 0.95 MPa.

23. The process as claimed in claim 12, wherein said heat transfer fluid of said stage c) is selected from $NaNO_3$-$NaNO_2$-$KNO_3$ eutectic mixtures.

24. The process as claimed in claim 1, wherein the ratio of the mass flow rate of said heat transfer fluid in the shell relative to the mass flow rate of said superheated feedstock introduced into said tubes is between 12 and 14.

* * * * *